(12) United States Patent
Cerier (10) Patent No.: US 7,846,180 B2
(45) Date of Patent: Dec. 7, 2010

(54) TISSUE FIXATION DEVICES AND METHODS OF FIXING TISSUE

(75) Inventor: Jeffrey C. Cerier, Franklin, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 987 days.

(21) Appl. No.: 10/677,633

(22) Filed: Oct. 2, 2003

(65) Prior Publication Data

US 2004/0133238 A1 Jul. 8, 2004

Related U.S. Application Data

(63) Continuation-in-part of application No. 09/859,579, filed on May 18, 2001, now Pat. No. 6,821,285, which is a continuation-in-part of application No. 09/574,424, filed on May 19, 2000, now Pat. No. 6,494,888, which is a continuation-in-part of application No. 09/520,273, filed on Mar. 7, 2000, now Pat. No. 6,663,639, and a continuation-in-part of application No. 09/519,945, filed on Mar. 7, 2000, now Pat. No. 6,506,196, said application No. 09/520,273, said application No. 09/519,945.

(60) Provisional application No. 60/460,308, filed on Apr. 4, 2003, provisional application No. 60/459,996, filed on Apr. 4, 2003, provisional application No. 60/140,492, filed on Jun. 22, 1999.

(51) Int. Cl.
*A61B 17/04* (2006.01)

(52) U.S. Cl. .................................. 606/232

(58) Field of Classification Search ............ 606/139, 606/142–144, 148, 151, 153–158, 213, 216, 606/219–221, 228, 232; 227/67, 68; 24/90.1, 24/93, 94, 102 FC, 114.7, 298; D24/145
See application file for complete search history.

(56) References Cited

U.S. PATENT DOCUMENTS 1,343,289 A 6/1920 Suchy (Continued)

FOREIGN PATENT DOCUMENTS

EP 0480428 4/1992

(Continued)

OTHER PUBLICATIONS

DeMeester, M.D. et al., "Nissen Fundoplication for Gastroesophageal Reflux Disease," Annals of Surgery, 204:9-20 (1986).

(Continued)

*Primary Examiner*—Julian W Woo (57) ABSTRACT

A tissue fixation device may include a suture, a first securing element connected to a first portion of the suture, and a second securing element connected to a second portion of the suture. The first and second securing elements are each rotatable from a first position during deployment of the tissue fixation device that is suitable for each securing element to pass through a respective hole formed in tissue to a second position when the tissue fixation device is deployed that inhibits each securing element from passing through the respective hole formed in the tissue. An exemplary method of fixing tissue may include creating two holes in the tissue and deploying a tissue fixation device having a suture connecting two securing elements by advancing each securing element through a respective hole in the tissue and causing each securing element to rotate to a position that inhibits the securing element from passing through the respective hole.

24 Claims, 7 Drawing Sheets

U.S. PATENT DOCUMENTS

| | | | |
|---|---|---|---|
| 1,548,250 A * | 8/1925 | Bobner | 24/94 |
| 2,104,885 A * | 1/1938 | Robbins | 24/114.7 |
| 2,199,025 A | 4/1940 | Conn | |
| 3,216,424 A | 11/1965 | William | |
| 3,399,432 A * | 9/1968 | Merser | 24/114.7 |
| 3,470,875 A | 10/1969 | Johnson | |
| 3,551,987 A | 1/1971 | Wilkinson | |
| 3,636,594 A * | 1/1972 | Faivre | 24/298 |
| 3,638,653 A | 2/1972 | Berry | |
| 3,734,375 A | 5/1973 | Bone et al. | |
| 3,749,085 A | 7/1973 | Willson et al. | |
| 3,842,840 A | 10/1974 | Schweizer | |
| 3,875,648 A | 4/1975 | Bone | |
| 3,900,925 A * | 8/1975 | La Torraca | 24/90.1 |
| 3,901,244 A | 8/1975 | Schweizer | |
| 3,933,291 A | 1/1976 | Stephenson | |
| 3,946,740 A | 3/1976 | Bassett | |
| 4,006,747 A | 2/1977 | Kronenthal et al. | |
| 4,014,492 A | 3/1977 | Rothfuss | |
| 4,043,504 A | 8/1977 | Hueil et al. | |
| 4,144,890 A | 3/1979 | Hess | |
| 4,164,225 A | 8/1979 | Johnson et al. | |
| 4,168,703 A | 9/1979 | Kenigsberg | |
| 4,177,818 A | 12/1979 | De Pedro | |
| 4,210,148 A | 7/1980 | Stivala | |
| 4,229,930 A * | 10/1980 | Ostermaier | 24/114.7 |
| 4,235,238 A | 11/1980 | Ogiu et al. | |
| 4,265,226 A | 5/1981 | Cassimally | |
| 4,375,866 A | 3/1983 | Giersch et al. | |
| 4,399,810 A | 8/1983 | Samuels et al. | |
| 4,407,286 A | 10/1983 | Noiles et al. | |
| 4,448,194 A | 5/1984 | DiGiovanni et al. | |
| 4,471,781 A | 9/1984 | Di Giovanni et al. | |
| 4,500,024 A | 2/1985 | DiGiovanni et al. | |
| 4,506,670 A | 3/1985 | Crossley | |
| 4,573,469 A | 3/1986 | Golden et al. | |
| 4,585,153 A | 4/1986 | Failla et al. | |
| 4,586,502 A | 5/1986 | Bedi et al. | |
| 4,591,085 A | 5/1986 | Di Giovanni | |
| 4,605,004 A | 8/1986 | Di Giovanni et al. | |
| 4,606,345 A | 8/1986 | Dorband et al. | |
| 4,607,638 A | 8/1986 | Crainich et al. | |
| 4,627,437 A | 12/1986 | Bedi et al. | |
| 4,635,637 A | 1/1987 | Schreiber | |
| 4,649,938 A | 3/1987 | McArthur | |
| 4,653,496 A | 3/1987 | Bundy et al. | |
| 4,665,906 A | 5/1987 | Jervis | |
| 4,669,473 A * | 6/1987 | Richards et al. | 606/232 |
| 4,696,300 A | 9/1987 | Anderson | |
| 4,705,040 A | 11/1987 | Mueller et al. | |
| 4,724,840 A | 2/1988 | McVay et al. | |
| 4,736,746 A | 4/1988 | Anderson | |
| 4,741,336 A | 5/1988 | Failla et al. | |
| 4,753,469 A | 6/1988 | Hiscott et al. | |
| 4,809,695 A | 3/1989 | Gwathmey et al. | |
| 4,841,888 A | 6/1989 | Mills et al. | |
| 4,862,359 A | 8/1989 | Trivedi et al. | |
| 4,880,015 A | 11/1989 | Nierman | |
| 4,887,612 A | 12/1989 | Esser et al. | |
| 4,890,615 A | 1/1990 | Caspari et al. | |
| 4,935,027 A | 6/1990 | Yoon | |
| 4,982,727 A | 1/1991 | Sato | |
| 5,015,249 A | 5/1991 | Nakao et al. | |
| 5,037,021 A | 8/1991 | Mills et al. | |
| 5,037,433 A | 8/1991 | Wilk et al. | |
| 5,040,715 A | 8/1991 | Green et al. | |
| 5,067,957 A | 11/1991 | Jervis | |
| 5,076,285 A | 12/1991 | Hess et al. | |
| 5,080,663 A | 1/1992 | Mills et al. | |
| 5,088,979 A | 2/1992 | Filipi et al. | |
| 5,147,373 A | 9/1992 | Ferzli | |
| 5,174,487 A | 12/1992 | Rothfuss et al. | |
| 5,190,546 A | 3/1993 | Jervis | |
| 5,219,359 A * | 6/1993 | McQuilkin et al. | 606/232 |
| 5,222,963 A | 6/1993 | Brinkerhoff et al. | |
| 5,230,344 A | 7/1993 | Ozdamar et al. | |
| 5,254,126 A | 10/1993 | Filipi et al. | |
| 5,289,963 A | 3/1994 | McGarry et al. | |
| 5,290,296 A | 3/1994 | Phillips | |
| 5,309,923 A | 5/1994 | Leuchter et al. | |
| 5,318,589 A | 6/1994 | Lichtman | |
| 5,324,325 A | 6/1994 | Moaddeb | |
| 5,331,969 A | 7/1994 | Silberstein | |
| 5,336,263 A | 8/1994 | Ersek et al. | |
| 5,346,504 A | 9/1994 | Ortiz et al. | |
| 5,350,391 A | 9/1994 | Iacovelli | |
| 5,354,311 A | 10/1994 | Kambin et al. | |
| 5,356,416 A | 10/1994 | Chu et al. | |
| 5,358,508 A | 10/1994 | Cobb et al. | |
| 5,364,408 A | 11/1994 | Gordon | |
| 5,376,095 A | 12/1994 | Ortiz | |
| 5,381,943 A | 1/1995 | Allen et al. | |
| 5,383,260 A * | 1/1995 | Deschenes et al. | 24/90.1 |
| 5,389,098 A | 2/1995 | Tsuruta et al. | |
| D356,154 S * | 3/1995 | Ferragamo | D24/145 |
| 5,395,030 A | 3/1995 | Kuramoto et al. | |
| 5,395,367 A | 3/1995 | Wilk | |
| 5,403,326 A | 4/1995 | Harrison et al. | |
| 5,433,721 A | 7/1995 | Hooven et al. | |
| 5,437,266 A | 8/1995 | McPherson et al. | |
| 5,441,507 A | 8/1995 | Wilk | |
| 5,447,512 A | 9/1995 | Wilson et al. | |
| 5,451,406 A | 9/1995 | Lawin et al. | |
| 5,464,426 A | 11/1995 | Bonutti | |
| 5,465,894 A | 11/1995 | Clark et al. | |
| 5,470,337 A | 11/1995 | Moss | |
| 5,485,952 A | 1/1996 | Fontayne | |
| 5,486,189 A | 1/1996 | Mudry et al. | |
| 5,496,331 A | 3/1996 | Xu et al. | |
| 5,522,820 A | 6/1996 | Caspari et al. | |
| 5,528,334 A | 6/1996 | Lee | |
| 5,538,008 A | 7/1996 | Crowe | |
| 5,549,618 A | 8/1996 | Fleenor et al. | |
| 5,558,665 A | 9/1996 | Kieturakis | |
| 5,571,090 A | 11/1996 | Sherts | |
| 5,571,116 A | 11/1996 | Bolanos et al. | |
| 5,573,496 A | 11/1996 | McPherson et al. | |
| 5,581,943 A | 12/1996 | Deren et al. | |
| 5,588,581 A | 12/1996 | Conlon et al. | |
| 5,597,378 A | 1/1997 | Jervis | |
| 5,613,499 A | 3/1997 | Palmer et al. | |
| 5,624,453 A | 4/1997 | Ahmed | |
| 5,626,613 A | 5/1997 | Schmieding | |
| 5,642,552 A | 7/1997 | Wang | |
| 5,645,552 A | 7/1997 | Sherts | |
| 5,662,683 A | 9/1997 | Kay | |
| 5,665,096 A | 9/1997 | Yoon | |
| 5,671,507 A * | 9/1997 | Deschenes et al. | 24/114.7 |
| 5,674,230 A | 10/1997 | Tovey et al. | |
| 5,676,674 A | 10/1997 | Bolanos et al. | |
| 5,697,940 A | 12/1997 | Chu et al. | |
| 5,699,808 A | 12/1997 | John | |
| 5,722,421 A | 3/1998 | Francese et al. | |
| 5,725,524 A | 3/1998 | Mulier et al. | |
| 5,728,109 A | 3/1998 | Schulze et al. | |
| 5,735,861 A | 4/1998 | Peifer et al. | |
| 5,741,280 A | 4/1998 | Fleenor | |
| 5,749,898 A | 5/1998 | Schulze et al. | |
| 5,787,897 A | 8/1998 | Kieturakis | |
| 5,788,138 A | 8/1998 | Deschenes et al. | |
| 5,792,153 A | 8/1998 | Swain et al. | |
| 5,792,478 A | 8/1998 | Lawin et al. | |
| 5,794,948 A | 8/1998 | Schmitt et al. | |
| 5,797,927 A | 8/1998 | Yoon | |

| Patent | Date | Inventor |
|---|---|---|
| 5,810,855 A | 9/1998 | Rayburn et al. |
| 5,810,882 A | 9/1998 | Bolduc et al. |
| 5,814,054 A | 9/1998 | Kortenbach et al. |
| 5,820,630 A | 10/1998 | Lind |
| 5,826,776 A | 10/1998 | Schulze et al. |
| 5,845,645 A * | 12/1998 | Bonutti ...................... 606/232 |
| 5,846,254 A | 12/1998 | Schulze et al. |
| 5,853,409 A | 12/1998 | Swanson et al. |
| 5,855,311 A | 1/1999 | Hamblin et al. |
| 5,887,594 A | 3/1999 | LoCicero, III |
| 5,893,592 A | 4/1999 | Schulze et al. |
| 5,897,562 A | 4/1999 | Bolanos et al. |
| 5,899,915 A | 5/1999 | Saadat |
| 5,901,895 A | 5/1999 | Heaton et al. |
| 5,954,731 A | 9/1999 | Yoon |
| 5,958,444 A | 9/1999 | Wallace et al. |
| 5,984,932 A | 11/1999 | Yoon |
| 5,993,466 A | 11/1999 | Yoon |
| 6,009,877 A | 1/2000 | Edwards |
| 6,051,003 A | 4/2000 | Chu et al. |
| 6,059,719 A | 5/2000 | Yamamoto et al. |
| 6,059,798 A | 5/2000 | Tolkoff |
| 6,067,990 A | 5/2000 | Kieturakis |
| 6,083,202 A | 7/2000 | Smith |
| 6,086,600 A | 7/2000 | Kortenbach |
| 6,086,603 A | 7/2000 | Termin et al. |
| 6,098,629 A | 8/2000 | Johnson et al. |
| 6,102,887 A | 8/2000 | Altman |
| 6,113,609 A | 9/2000 | Adams |
| 6,129,761 A | 10/2000 | Hubbell |
| RE36,974 E * | 11/2000 | Bonutti ...................... 606/232 |
| 6,152,935 A | 11/2000 | Kammerer et al. |
| 6,159,146 A | 12/2000 | El Gazayerli |
| 6,179,840 B1 | 1/2001 | Bowman |
| 6,221,084 B1 | 4/2001 | Fleenor |
| 6,238,335 B1 | 5/2001 | Silverman et al. |
| 6,254,642 B1 | 7/2001 | Taylor |
| 6,258,064 B1 | 7/2001 | Smith et al. |
| 6,267,285 B1 | 7/2001 | Raymond et al. |
| 6,312,437 B1 | 11/2001 | Kortenbach |
| 6,312,448 B1 | 11/2001 | Bonutti |
| 6,315,184 B1 | 11/2001 | Whitman |
| 6,325,503 B1 | 12/2001 | McCue, Jr. et al. |
| 6,352,503 B1 | 3/2002 | Matsui et al. |
| 6,387,104 B1 | 5/2002 | Pugsley, Jr. et al. |
| 6,443,973 B1 | 9/2002 | Whitman |
| 6,454,778 B2 | 9/2002 | Kortenbach |
| 6,461,366 B1 | 10/2002 | Seguin |
| 6,478,210 B2 | 11/2002 | Adams et al. |
| 6,494,888 B1 | 12/2002 | Laufer et al. |
| 6,506,196 B1 | 1/2003 | Laufer |
| 6,540,789 B1 | 4/2003 | Silverman et al. |
| 6,544,291 B2 | 4/2003 | Taylor |
| 6,544,503 B1 | 4/2003 | Vanderhoff et al. |
| 6,547,776 B1 | 4/2003 | Gaiser et al. |
| 6,548,501 B2 | 4/2003 | Hakkinen |
| 6,548,518 B2 | 4/2003 | Rubin et al. |
| 6,551,315 B2 | 4/2003 | Kortenbach et al. |
| 6,551,328 B2 | 4/2003 | Kortenbach |
| 6,552,045 B2 | 4/2003 | Rubin et al. |
| 6,552,046 B2 | 4/2003 | Druzgala et al. |
| 6,552,047 B2 | 4/2003 | Garvey et al. |
| 6,558,400 B2 | 5/2003 | Deem et al. |
| 6,558,429 B2 | 5/2003 | Taylor |
| 6,559,165 B1 | 5/2003 | Rubin et al. |
| 6,562,034 B2 | 5/2003 | Edwards et al. |
| 6,562,795 B2 | 5/2003 | Ashley et al. |
| 6,569,085 B2 | 5/2003 | Kortenbach et al. |
| 6,569,105 B1 | 5/2003 | Kortenbach et al. |
| 6,572,626 B1 | 6/2003 | Knodel et al. |
| 6,575,971 B2 | 6/2003 | Hauck et al. |
| 6,579,301 B1 | 6/2003 | Bales et al. |
| 6,589,238 B2 | 7/2003 | Edwards et al. |
| 6,591,137 B1 | 7/2003 | Fischell et al. |
| 6,591,838 B2 | 7/2003 | Durgin |
| 6,592,596 B1 | 7/2003 | Geitz |
| 6,592,609 B1 * | 7/2003 | Bonutti ...................... 606/232 |
| 6,595,909 B2 | 7/2003 | Silverman et al. |
| 6,595,910 B2 | 7/2003 | Silverman et al. |
| 6,604,004 B1 | 8/2003 | Zelickson et al. |
| 6,604,528 B1 | 8/2003 | Duncan |
| 6,605,078 B2 | 8/2003 | Adams |
| 6,609,140 B1 | 8/2003 | Greene |
| 6,613,047 B2 | 9/2003 | Edwards |
| 6,632,227 B2 | 10/2003 | Adams |
| 6,645,201 B1 | 11/2003 | Utley et al. |
| 6,652,545 B2 | 11/2003 | Shipp et al. |
| 6,660,301 B1 | 12/2003 | Vogel et al. |
| 6,663,639 B1 | 12/2003 | Laufer et al. |
| 6,666,848 B2 | 12/2003 | Stone |
| 6,669,713 B2 | 12/2003 | Adams |
| 6,673,058 B2 | 1/2004 | Snow |
| 6,673,070 B2 | 1/2004 | Edwards et al. |
| 6,692,507 B2 | 2/2004 | Pugsley et al. |
| 6,695,764 B2 | 2/2004 | Silverman et al. |
| 6,695,866 B1 | 2/2004 | Kuehn et al. |
| 6,699,243 B2 | 3/2004 | West et al. |
| 6,712,074 B2 | 3/2004 | Edwards et al. |
| 6,712,814 B2 | 3/2004 | Edwards et al. |
| 6,716,226 B2 | 4/2004 | Sixto, Jr. et al. |
| 6,716,233 B1 | 4/2004 | Whitman |
| 6,725,866 B2 | 4/2004 | Johnson et al. |
| 6,743,240 B2 | 6/2004 | Smith et al. |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,793,652 B1 | 9/2004 | Whitman et al. |
| 6,808,491 B2 | 10/2004 | Kortenbach et al. |
| 6,821,285 B2 | 11/2004 | Laufer et al. |
| 6,824,548 B2 | 11/2004 | Smith et al. |
| 6,835,200 B2 | 12/2004 | Laufer et al. |
| 6,843,403 B2 | 1/2005 | Whitman |
| 6,843,794 B2 | 1/2005 | Sixto, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,916,332 B2 | 7/2005 | Adams |
| 6,926,722 B2 | 8/2005 | Geitz |
| 6,945,979 B2 | 9/2005 | Kortenbach et al. |
| 6,971,395 B2 | 12/2005 | Edwards et al. |
| 6,981,941 B2 | 1/2006 | Whitman et al. |
| 6,986,737 B2 | 1/2006 | Suzuki et al. |
| 7,032,798 B2 | 4/2006 | Whitman et al. |
| 7,033,370 B2 | 4/2006 | Gordon et al. |
| 7,066,944 B2 | 6/2006 | Laufer et al. |
| 7,077,856 B2 | 7/2006 | Whitman |
| 7,087,073 B2 * | 8/2006 | Bonutti ...................... 606/232 |
| 7,153,314 B2 | 12/2006 | Laufer et al. |
| 2001/0049537 A1 | 12/2001 | Kortenbach |
| 2001/0056282 A1 | 12/2001 | Sonnenschein et al. |
| 2002/0010418 A1 | 1/2002 | Lary et al. |
| 2002/0022851 A1 | 2/2002 | Kalloo et al. |
| 2002/0063143 A1 | 5/2002 | Adams et al. |
| 2002/0068945 A1 | 6/2002 | Sixto, Jr. et al. |
| 2002/0068946 A1 | 6/2002 | Kortenbach et al. |
| 2002/0078967 A1 | 6/2002 | Sixto, Jr. et al. |
| 2002/0082621 A1 | 6/2002 | Schurr et al. |
| 2002/0138086 A1 | 9/2002 | Sixto, Jr. et al. |
| 2002/0173786 A1 | 11/2002 | Kortenbach et al. |
| 2002/0193816 A1 | 12/2002 | Laufer et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |

| | | | |
|---|---|---|---|
| 2002/0198541 A1 | 12/2002 | Smith et al. | |
| 2002/0198549 A1 | 12/2002 | Sixto et al. | |
| 2003/0019905 A1 | 1/2003 | Adams et al. | |
| 2003/0036679 A1 | 2/2003 | Kortenbach et al. | |
| 2003/0065340 A1 | 4/2003 | Geitz | |
| 2003/0065359 A1 | 4/2003 | Weller et al. | |
| 2003/0068326 A1 | 4/2003 | Gevas et al. | |
| 2003/0069280 A1 | 4/2003 | Koch et al. | |
| 2003/0069646 A1 | 4/2003 | Stinson | |
| 2003/0083241 A1 | 5/2003 | Young | |
| 2003/0086968 A1 | 5/2003 | Gray | |
| 2003/0092699 A1 | 5/2003 | Uchida et al. | |
| 2003/0130560 A1 | 7/2003 | Suzuki et al. | |
| 2003/0130561 A1 | 7/2003 | Suzuki et al. | |
| 2003/0135206 A1 | 7/2003 | Edwards et al. | |
| 2003/0161887 A1 | 8/2003 | Klein | |
| 2003/0163029 A1 | 8/2003 | Sonnenschein et al. | |
| 2003/0167062 A1 | 9/2003 | Gambale et al. | |
| 2003/0171645 A1 | 9/2003 | Silverman et al. | |
| 2003/0181929 A1 | 9/2003 | Geitz | |
| 2003/0188755 A1 | 10/2003 | Milbocker | |
| 2003/0191478 A1 | 10/2003 | Kortenbach et al. | |
| 2003/0192558 A1 | 10/2003 | Durgin | |
| 2003/0192559 A1 | 10/2003 | Durgin | |
| 2003/0195387 A1 | 10/2003 | Kortenbach et al. | |
| 2003/0195509 A1 | 10/2003 | Edwards et al. | |
| 2003/0196670 A1 | 10/2003 | Durgin | |
| 2003/0199731 A1 | 10/2003 | Silverman et al. | |
| 2003/0208209 A1 | 11/2003 | Gambale et al. | |
| 2003/0208211 A1 | 11/2003 | Kortenbach | |
| 2003/0216754 A1 | 11/2003 | Kraemer et al. | |
| 2003/0220657 A1 | 11/2003 | Adams | |
| 2003/0220660 A1 | 11/2003 | Kortenbach et al. | |
| 2003/0236535 A1 | 12/2003 | Onuki et al. | |
| 2003/0236536 A1 | 12/2003 | Grigoryants et al. | |
| 2004/0006336 A1 | 1/2004 | Swanson | |
| 2004/0006351 A1 | 1/2004 | Gannoe et al. | |
| 2004/0010245 A1 | 1/2004 | Cerier et al. | |
| 2004/0037887 A1 | 2/2004 | Bourne et al. | |
| 2004/0044364 A1 | 3/2004 | DeVries et al. | |
| 2004/0059349 A1 | 3/2004 | Sixto et al. | |
| 2004/0059350 A1 | 3/2004 | Gordon et al. | |
| 2004/0059354 A1 | 3/2004 | Smith et al. | |
| 2004/0059358 A1 | 3/2004 | Kortenbach et al. | |
| 2004/0082859 A1 | 4/2004 | Schaer | |
| 2004/0082950 A1 | 4/2004 | Edwards et al. | |
| 2004/0082963 A1 | 4/2004 | Gannoe et al. | |
| 2004/0116948 A1 | 6/2004 | Sixto et al. | |
| 2004/0133238 A1 | 7/2004 | Cerier | |
| 2004/0147943 A1 | 7/2004 | Kobayashi | |
| 2004/0153107 A1 | 8/2004 | Kayan et al. | |
| 2004/0162568 A1 | 8/2004 | Saadat et al. | |
| 2004/0176783 A1 | 9/2004 | Edoga et al. | |
| 2004/0193184 A1 | 9/2004 | Laufer et al. | |
| 2004/0193193 A1 | 9/2004 | Laufer et al. | |
| 2004/0193194 A1 | 9/2004 | Laufer et al. | |
| 2004/0194790 A1 | 10/2004 | Laufer et al. | |
| 2005/0033320 A1 | 2/2005 | McGuckin et al. | |
| 2005/0033328 A1 | 2/2005 | Laufer et al. | |
| 2005/0216036 A1 | 9/2005 | Nakao | |
| 2006/0025789 A1 | 2/2006 | Laufer et al. | |
| 2009/0198254 A1 | 8/2009 | Laufer et al. | |

FOREIGN PATENT DOCUMENTS

| | | | |
|---|---|---|---|
| EP | 0576265 | | 12/1993 |
| EP | 0593920 | | 4/1994 |
| EP | 0646356 | | 4/1995 |
| EP | 0668058 | | 8/1995 |
| EP | 0743044 | | 11/1996 |
| EP | 0975263 | | 2/2000 |
| FR | 2768324 | | 3/1999 |
| GB | 2075829 | * | 11/1981 |
| GB | 2075829 A | * | 11/1981 |
| JP | 61122852 | | 6/1986 |
| JP | 1151461 | | 6/1989 |
| JP | 05103241 A | | 4/1993 |
| JP | 05323412 A | | 12/1993 |
| JP | 08006102 A | | 1/1996 |
| JP | 2000254143 A | | 9/2000 |
| JP | 2001507972 T | | 6/2001 |
| JP | 2003051982 A | | 2/2003 |
| JP | 2006311060 A | | 11/2006 |
| WO | 8911827 | | 12/1989 |
| WO | WO-8911827 | | 12/1989 |
| WO | WO-9529635 A1 | | 11/1995 |
| WO | 9627345 A2 | | 9/1996 |
| WO | WO-9803151 | | 1/1998 |
| WO | WO-9900059 | | 1/1999 |
| WO | WO 99/22649 | | 5/1999 |
| WO | WO 99/60931 | | 12/1999 |
| WO | WO-0035529 | | 6/2000 |
| WO | WO 00/78227 | | 12/2000 |
| WO | WO-0078227 | | 12/2000 |
| WO | WO-0078229 | | 12/2000 |
| WO | WO-01085034 | | 11/2001 |
| WO | WO-0224080 | | 3/2002 |
| WO | WO-0228289 | | 4/2002 |
| WO | WO-0240081 | | 5/2002 |
| WO | WO-0245603 | | 6/2002 |
| WO | WO-02076541 | | 10/2002 |
| WO | WO 02/094341 | | 11/2002 |
| WO | WO-02094341 | | 11/2002 |
| WO | WO 03/000115 | | 1/2003 |
| WO | WO 03/007796 | | 1/2003 |
| WO | WO-03004087 | | 1/2003 |
| WO | WO-03015604 | | 2/2003 |
| WO | WO-03030782 | | 4/2003 |
| WO | WO-03035649 | | 5/2003 |
| WO | WO-03037256 | | 5/2003 |
| WO | WO 03/053253 | | 7/2003 |
| WO | WO-03072196 | | 9/2003 |
| WO | WO-03082359 | | 10/2003 |
| WO | 03096885 A2 | | 11/2003 |
| WO | WO 03/090633 | | 11/2003 |
| WO | WO 03/092509 | | 11/2003 |
| WO | WO-03092498 | | 11/2003 |
| WO | WO-03094800 | | 11/2003 |
| WO | WO-03096885 | | 11/2003 |
| WO | WO-03098885 | | 11/2003 |
| WO | WO 03/099137 | | 12/2003 |
| WO | WO 03/099139 | | 12/2003 |
| WO | WO 03/099140 | | 12/2003 |
| WO | WO 2004/000129 | | 12/2003 |
| WO | WO-03099376 | | 12/2003 |
| WO | WO-03105917 | | 12/2003 |
| WO | WO 2004/004542 | | 1/2004 |
| WO | WO-2004004544 | | 1/2004 |
| WO | WO-2004006990 | | 1/2004 |
| WO | WO 2004/019787 | | 3/2004 |
| WO | WO 2004/019788 | | 3/2004 |
| WO | WO 2004/021872 | | 3/2004 |
| WO | WO 2004/021873 | | 3/2004 |
| WO | WO 2004/021894 | | 3/2004 |
| WO | WO 2004/026348 | | 4/2004 |
| WO | WO 2004/026349 | | 4/2004 |
| WO | WO 2004/026350 | | 4/2004 |
| WO | WO-2005086885 | | 9/2005 |

OTHER PUBLICATIONS

Boerema, M.D., "Hiatus hernia: Repair by right-sided, subhepatic, anterior gastropexy," *Surgery*, 65:884-893 (1969).

Carvalho PJPC et al., Fibrosis of gastric cardia after endoscopic sclerosis. Mechanism for control of experimental reflux? *Am. Surg.* 1990 Mar. 56(3):163-6.

Cecconello, "Esophagogastric Anastomosis with Valvuloplasty: An Experimental Study," *International Surgery*, 67:121-124 (1982).

Collis, M.D., "An Operation for Hiatus Hernia with Short Esophagus" *The Journal of Thoracic Surgery* 34:768-778 (1957).

Collis, M.D., "Surgical Control of Reflux in Hiatus Hernia," *The American Journal of Surgery*, 115:465-471 (1968).

Contractor QQ et al., Endoscopic esophagitis and gastroesophageal flap valve, *J. Clin Castroenterol* 1999, Apr. 28(3):233-7.

Cuschieri, et al., "Multicenter prospective evaluation of laparoscopic antireflux surgery," *Surgical Endoscopy*, 7:505-510 (1993).

Digestive Disease Week, Orange County Convention Center, p. A-802; 314*.

Donahue PE et al., Endoscopic control of gastro-esophageal reflux: status report, *World J. Surg.* 1992 Mar.-Apr. 16(2):343-6.

Donahue PE et al., Endoscopic sclerosis of the gastric cardia for prevention of experimental gastroesophageal reflux, *Gastrointest. Endosc.* 1990 May-Jun. 36(3):253-6.

European Search Report mailed Sep. 2, 2004, in EP Application No. 04076389.

Eurpoean Search Report mailed Jul. 10, 2007 in EP Application No. 07075291.

Falk, et al., "Laparoscopic Fundoplication: A preliminary report of the technique and postoperative care," *Aust. N.Z.J. Surgery*, 62:969-972 (1992).

Hill LD and Kozarek RA, The gastroesophageal flap valve, *J. Clin. Gastroenterol* 1999 Apr. 28(3): 194-7.

Hill LD et al., Antireflux surgery. A surgeon's look, *Gastroenterol Clin. North Am.*, Sep. 1990 19(3):745-75.

Hill LD et al., The gastroesophageal flap valve: in vitro and in vivo observations. *Gastrointest. Endosc.* 1996 Nov. 44(5):541-7.

Hill LD, Intraoperative measurement of lower esophageal sphicter pressure, *J. Thorac Cardiovasc. Surg.* 1978 Mar. 75(3):378-82.

Hill LD, Myths of the esophagus, *J. Thorac Cardiovasc. Surg.* 1989 Jul. 9S(1):1-10.

Hill, et al., "Surgery for Peptic Esophageal Stricture," 139-147.

Hill, et al., "The Esophagus. Medical and Surgical Management," *WB Saunders Co.*, 135-8 (1988).

Hill, M.D., "An Effective Operation for Hiatal Hernia: An Eight Year Appraisal," *Annals of Surgery*, 166:681-692 (1967).

Hinder et al., "The surgical option for gastroesophageal reflux disease," Symposium on gastroesophageal reflux disease, AM J. Med., 103: 1445-1485, 1997.

International Search Report dated Oct. 16, 2000.

Ismail T. et al., Yield pressure, anatomy of the cardia and gastro-oesophageal reflux, *Br. J. Surg.* 1995 Jul. 82(7):943-7.

Ismail, et al., "Yield Pressure: A New Concept in the Evaluation of Gerd?," *AJG*, 91:616-617 (1996).

Jamieson, et al., "Laparoscopic Nissen Fundoplication," *Annals of Surgery*, 220:137-145 (1994).

Jamieson, et al., "The development of surgery for gastro-oesophageal reflux disease." *Surgery of the Oesophagus*, 233-245 (1988).

Janssen, et al., "Prospective randomized comparison of teres cardiopexy and Nissen fundoplication in the surgical therapy of gastro-oesophageal reflux disease." *Br. J. Surq.*, 80:875-878 (1993).

Jennings, et al., "A Novel Endoscopic Transgastric Fundoplication Procedure for Gastroesophageal Reflux: An Initial Animal Evaluation," *Journal of Laparoendoscopic Surgery*, 2:207-213 (1992).

Kadirkamanathan SS et al., An ambulant porcine model of acid reflux used to evaluate endoscopic gastroplasty. *Gut.* 1999 Jun. 44(6):782-8.

Kadirkamanathan SS et al., Antireflux operations at flexible endoscopy using endoluminal stitching techniques: an experimental study, *Gastrointest. Endosc.* 1996 Aug. 44(2):133-43.

Kahrilas, "Gastroesophageal Reflux Disease," *JAMA*, 276:983-988 (1996).

Kraemer, M.D., et al., "Laparoscopic Hill repair," *Gastrointestinal Endoscopy*, 40:155-159 (1994).

Little, M.D., "Mechanisms of Action of Antireflux Surgery: Theory and Fact" *World Journal of Surgery*, 16:320-325 (1992).

Mason RJ et al., A new intraluminal antigastroesophageal reflux procedure in baboons, *Gastrointest. Endosc.* 1997 Mar. 45(3):283-90.

Mason, et al., "Nissen Fundoplication Prevents Shortening of the Sphicter During Gastric Distention," *Arch Surg.*, 132:719-726 (1997).

McGouran RC et al., Does measurement of yield pressure at the cardia during endoscopy provide information on the function of the lower oesophageal sphicter mechanism? *Gut* 1988 Mar. 29(3):275-8.

McGouran RC et al., Is yield pressure at the cardia increased by effective fundoplication? *Gut* 1989 Oct. 30(10): 1309-12.

McGouran, M.D., et al., "A laser-induced scar at the cardia increases the yield pressure of the lower esophageal sphicter." *Gastronintestinal Endoscopy*, 36:439-443 (1990).

McKernan, "Laparoscopic repair of gastroesophageal reflux disease," *Surgical Endoscopy*, 8:851-856 (1994).

Nathanson, et al., "Laparoscopic Ligamentum teres (round ligament) cardiopexy," *Br. J. Surg.*, 78:947-951 (1991).

Nissen, "Eine einfache Operation zur Beeinflussung der Refluxoesophagitis " *Journal Suisee DeMedecine*, 590-592 (1956).

O'Connor KW and Lehman GA, Endoscopic placement of collagen at the lower esophageal sphicter to inhibit gastroesophageal reflux: a pilot study of 10 medically intractable patients. *Gastrointest. Endosc.* 1988 Mar.-Apr. 34(2):106-12.

O'Connor KW et al., An experimental endoscopic technique for reversing gastroesophageal reflux in dogs by injecting inert material in the distal esophagus. *Gastrointest. Endosc.* 1984 Oct. 30(5):275-80.

Pedinielli, "Traitement Chirurgical de la Herinie Hiatale Par La Technique du Collet," *Ann. Chir.* 18:1461-1474 (1964). (English Abstract).

Nissen, "Eine einfache Operation zur Beeinflussung der Refluxoesophagitis," *Journal Suisee DeMedecine*, 590-592 (1956).

Polk, et al., "Hiatol Hernia and Esophagitis: A survey of indications for operation and technic and results of fundoplication," *Ann. Surg.*, 173:775-781 (1971).

Rampal, et al., "Technique Chirurgicale, Traitement des hernies hiatales et du reflux aesophagien par la cardio-pexie avec le ligament round de foie," *La Presse Medicale*, 75:617-619 (1967).

Rich, "Simple GERD Treatment Offers New Alternative" (www.medicalpost.com website), Mar. 1999.

Rupp TH and Lehman GA, Endoscopic antireflux techniques. Endoluminal and laparoscopic. *Gastrointest. Endosc. Clin. N. Am.* Apr. 1994 4(2):353-68.

Shafik A., Intraesophageal Polytef injection for the treatment of reflux esophagitis. *Surg. Endosc.* Mar. 1996 10(3):329-31.

Singh et al., "Evaluation of the Endoscopic Suturing System in the Treatment of the GERD," Conference Abstract for Plenary Session for Digestive Disease Week, p. 314 & A-802, May 16-19, 1999.

Skinner, et al., "Surgical management of esophageal reflux and hiatus hernia " *Journal of Thoracic and Cardiovascular Surgery*, 53:33-54 (1967).

Slim K. et al., Intraoperative esophageal manometry and fundoplications: prospective study. *World J. Surg.* Jan. 1996 20(1):55-9.

Starling, et al., Assessment of the Angelchik Prosthesis for Treatment of Symptomatic Esophageal Reflux, *World J. Surg.*, 11, 350-355 (1987).

The Americal journal of gastroenterology, vol. 91, No. 3, 1996, pp. 616-617.

Thor KBA et al., Reappraisal of the flap valve mechanism in the gastroesophageal junction. A study of a new valvuloplasty procedure in cadavers. *Acta Chir Scand* Jan. 1987 153(1):25-8.

Tocornal, M.D., et al., A mucosol flap valve mechanism to prevent gastroesophageal reflux and esophagitis, *Surgery*, 64:519-523 (1968).

Wang, et al., "A new anti-flux procedure: cardiac oblique invagination," *Chung Hua Wai Ko Tsa Chih*, Feb. 33 (2) 73-5 (1995). (English Abstract).

Watson, et al., "Comparison of anterior, posterior and total fundoplication using a viscera model," *Diseases of the Esophagus*, 10:110-114 (1997).

Westbrook, et al., "Posterior Surgical Approaches to the Rectum," *Annals of Surgery*, 195:677-691 (1982).

Japanese Preliminary Report (Application No. 2004-506665) dated Mar. 31, 2009.

Extended European Search Report (Application No. EP 07 07 5291) dated Oct. 7, 2007.
McGouran RC et al., Is yield pressure at the cardia increased by effective fundoplication? Gut Oct. 1989; 30(10): 1309-12.
Donahue, M.D., et al. "Endoscopic Control of Gastro-Esophageal Reflux: Status Report," World Journal of Surgery, 16:343-346 (1992).
Starling et al., "Treatment of Symptomatic Gastroesophageal Reflux Using the Angelchika Prosthesis," Ann. Surg. (1982) 686:690.
Japanese Preliminary Report (Application No. 2004-506665) dated Mar. 31, 2009.
Feb. 17, 2009, Office Action for U.S. Appl. No. 10/819,996.
Feb. 20, 2009, Office Action for U.S. Appl. No. 10/819,957.
Dodds WJ et al. 1982, N Engl J Med 307:1547-52.
European Office Action dated Apr. 3, 2009 in EP07075291.0.
European Office Action dated Feb. 11, 2010 in EP03 728 882.6.
European Office Action dated Sep. 11, 2009 in EP05 077 998.2.
Hetzel DJ et al. 1988, Gastroenterology 95:903-12.
Japanese Office Action for Application No. 2005-122394 dated May 12, 2009.
Klinkenberg-Knol EC and Meuwissen SG 1988, Aliment Pharmacol Ther 2:221-7.
Klinkenberg-Knol EC and Meuwissen SG 1989, Digestion 1:47-53.
Lambert R at al. 1993, Gastroenterology 104:1554-7.
Moss Tubes advertisement, *Annals of Surgery*, vol. 220, No. 2, Aug, 1994 (2 pages).
O'Connor, et al., "Endoscopic placement of collagen at the lower esophageal sphicter to inhibit gastroesophageal reflux: a pilot study of 10 medically intractable patients," *Gastrointestinal Endoscopy*, 34:106-112 (1988).
Poynter D at al. 1985, Gut 26:1284-95.
Solcia E at al. 1993, Aliment Pharmacol Ther 7(supp. 1):25-8.
Spechler SJ 1992, N Engl J Med 326:786-92.
Japanese Office Action for Application No. 2004-131922 dated Jan. 18, 2010 (English translation).

* cited by examiner

FIG. 18

TISSUE FIXATION DEVICES AND METHODS OF FIXING TISSUE

CROSS-REFERENCE TO RELATED APPLICATIONS

This application claims the benefit of provisional application U.S. Ser. No. 60/460,308, filed Apr. 4, 2003, and also claims the benefit of provisional application U.S. Ser. No. 60/459,996, filed Apr. 4, 2003. This application is a continuation-in-part of application U.S. Ser. No. 09/859,579, filed May 18, 2001, now U.S. Pat. No. 6,821,285, which is itself a continuation-in-part of application U.S. Ser. No. 09/574,424, filed May 19, 2000, now U.S. Pat. No. 6,494,888, which is a continuation-in-part both of application U.S. Ser. No. 09/520,273, filed Mar. 7, 2000, now U.S. Pat. No. 6,663,639, and of application U.S. Ser. No. 09/519,945, filed Mar. 7, 2000, now U.S. Pat. No. 6,506,196, both of which claim the benefit of provisional application U.S. Ser. No. 60/140,492, filed Jun. 22, 1999. All of the above-listed applications are hereby incorporated herein by reference in their entireties.

BACKGROUND

This subject matter relates to methods and apparatus for reconfiguring tissue, and more particularly to reconfiguring tissue in the vicinity of the gastroesophageal junction.

Gastroesophageal reflux disease (GERD) is a common upper-gastrointestinal disorder in which acidic contents of the stomach flow inappropriately from the stomach into the esophagus. Backflow of gastric contents into the esophagus results, for example, when gastric pressure is sufficient to overcome the resistance to flow that normally exists at the gastroesophageal junction (GEJ) or when gravity acting on the contents is sufficient to cause flow through the GEJ. Medication, open surgical procedures, minimally invasive surgical techniques, and endoscopic techniques are known for treating GERD.

SUMMARY

The present disclosure describes tissue fixation devices and methods of fixing tissue that allow tissue to be reliably fixed with minimal effort by the medical practitioner. For example, certain exemplary embodiments of the tissue fixation devices disclosed herein may be deployed without requiring the physician to tie suture knots during deployment. The tissue fixation devices and methods disclosed herein may be used to secure, anchor, or otherwise fix tissue in a wide variety of surgical, endoscopic, or other medical procedures, including the closing of surgical sites or the closing of trauma wounds. The tissue fixation devices and methods disclosed herein are particularly suited for use in trans-oral surgical procedures, such as the treatment of GERD and in connection with surgical procedures that result in reconfiguration of tissue.

In one aspect, the disclosure describes a tissue fixation device including a suture, a first securing element connected to a first portion of the suture, and a second securing element connected to a second portion of the suture. The first and second securing elements are each rotatable from a first position during deployment of the tissue fixation device that is suitable for each securing element to pass through a respective hole formed in tissue to a second position when the tissue fixation device is deployed that inhibits each securing element from passing through the respective hole formed in the tissue.

In certain exemplary embodiments, a tissue fixation device may include a suture, a first pledget having at least one through hole formed therein, a first portion of the suture passing through the at least one through hole in the first pledget and a second portion of the suture configured to inhibit the second portion from passing through the at least one through hole in the first pledget, a second pledget having at least one through hole formed therein, the first pledget being spaced apart from the second pledget to receive tissue therebetween when the tissue fixation device is deployed, a first securing element connected to a portion of the suture, the first securing element being rotatable from a first position in which the securing element is oriented at least substantially parallel to the at least one through hole formed in the first pledget and the second pledget to a second position in which the securing element is oriented at least substantially perpendicular to the at least one through hole in the second pledget.

In other exemplary embodiments, a tissue fixation device may include a suture, and a first securing element having a proximal end and a distal end, the first securing element being coupled to a first portion of the suture, the distal end of the first securing element having a sharp tip, the proximal end of the first securing element being configured for removable attachment to a deployment instrument, the first securing element being configured to secure the tissue fixation device to a distal side of tissue, the suture having a proximal portion configured to secure the tissue fixation device at a proximal side of the tissue, the tissue being fixed between the first securing element and the proximal portion of the suture during deployment.

In another aspect, a tissue fixation device may include a suture, a first pledget having a plurality of through holes formed therein, the suture passing through the through holes in the first pledget, a second pledget having a plurality of through holes formed therein, the first pledget being spaced apart from the second pledget to receive tissue therebetween when the tissue fixation device is deployed, a first securing element having a sharp tip and a proximal end configured for removable attachment to an instrument, the first securing element being coupled to the suture, and a second securing element having a sharp tip and a proximal end configured for removable attachment to an instrument, the second securing element being coupled to the suture.

A method of fixing tissue may include creating two holes in the tissue, and deploying a tissue fixation device having a suture connecting two securing elements by advancing each securing element through a respective hole in the tissue, and causing each securing element to rotate to a position that inhibits the securing element from passing through the respective hole.

In an embodiment, a method of fixing tissue with a tissue fixation device having a suture connected to a securing element, may include creating a hole in the tissue by advancing the securing element through the tissue using a deployment instrument, and deploying the tissue fixation device by separating the securing element from the deployment instrument, and configuring the securing element to inhibit the securing element from passing through the hole.

BRIEF DESCRIPTION OF THE DRAWINGS

These and other features disclosed herein will be more fully understood by reference to the following detailed description in conjunction with the attached drawings in which like reference numerals refer to like elements through the different views. The drawings illustrate features of the tissue fixation devices disclosed herein and, although not to scale, show relative dimensions.

DETAILED DESCRIPTION OF EXEMPLARY EMBODIMENTS

Figure 1:
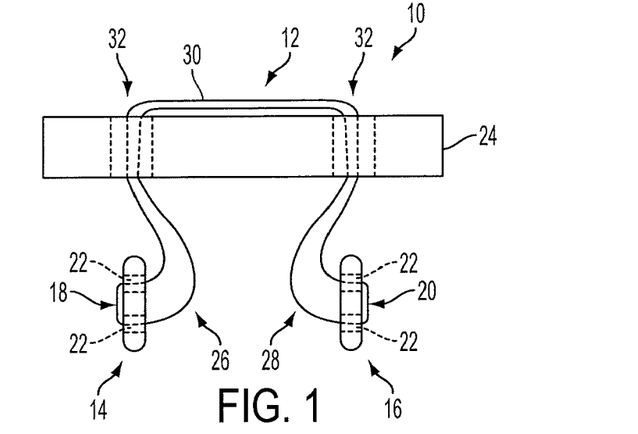
FIG. 1 is a side elevational view of an exemplary embodiment of a tissue fixation device, illustrating the securing elements of the device in first position suitable for deployment of the device.
Figure 2:
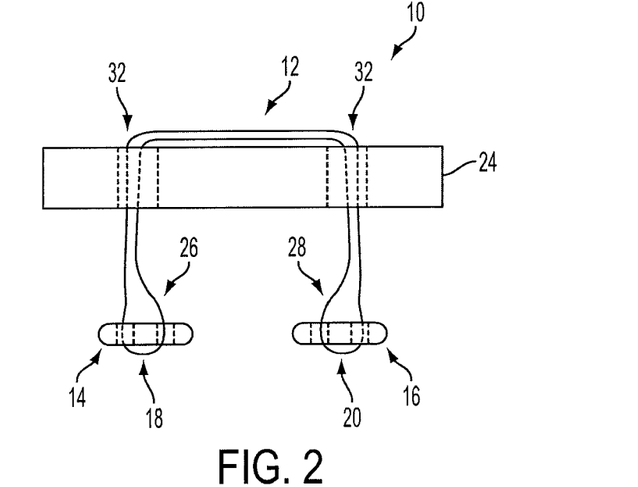
FIG. 2 is a side elevational view of the tissue fixation device of FIG. 1, illustrating the securing elements of the device is a second position that anchors the device within the tissue.

FIGS. 1 and 2 illustrate an exemplary embodiment of a tissue fixation device 10 including a suture 12, a first securing element 14, and a second securing element 16. The first securing element 14 may be connected to a first portion 18 of the suture 12 and the second securing element 16 may be connected to a second portion 20 of the suture 12. In this exemplary embodiment, the first securing element 18 and the second securing element 16 are generally cylindrical in shape and each include a pair of openings 22. Each pair of openings 22 receives a respective loop 26, 28 of suture 12 and thereby connects the suture 12 to the securing elements 14 and 16. Thus, the first portion 18 of the suture 12 can loop through openings 22 in the first securing element 14. Similarly, the second portion 20 of the suture 12 can loop through openings 22 in the second securing element 16. In one exemplary embodiment, strands of the suture 12 can pass through holes in the tissue. Securing elements 14, 16 may be elongated and may be substantially cylindrical in shape as illustrated in FIG. 1, but could have a variety of shapes as described below.

The suture 12 may also have a third portion 30. In the illustrated embodiment, the third portion 30 is continuous (i.e., the suture 12 may be an endless loop of suture). The third portion 30 of the suture 12 may alternatively include two ends of the suture 12. The portions may be loose or affixed to one another. The portions may be coupled to each other in a variety of ways. For example, the portions may be coupled by knotting; by welding; by gluing; by being melted together; by being braided together; by being both attached to a connector; and/or by being stapled together. Other types of affixation can be readily envisioned by one of requisite skill in the art. Thus, the suture may form a closed loop.

A wide variety of materials can be used to form the suture. In an embodiment, the suture can be USP size 2-0 monofilament polypropylene. Likewise, a wide variety of materials can be used to form the securing elements. In an embodiment, the securing elements can be formed at least in part of titanium.

When the tissue fixation device is deployed or is being deployed, the first and second securing elements 14 and 16 can be spaced apart from the third portion 30 of the suture 12 such that the tissue to be fixed by the device is located between the securing elements 14, 16 and the third portion 30 of the suture 12. In an embodiment, the spacing between securing elements 14, 16 may be from about 1 mm to about 20 mm, preferably about 6 mm to about 8 mm. The amount of space between the securing elements 14, 16, and the third portion 30 of the suture 12 can be selected to facilitate, for example, fixation of tissue having particular dimensions. The space can also be adjusted during deployment to facilitate delivery of the device. For example, the spacing can be large initially to facilitate positioning of the device on or around the tissue to be fixed. The space can subsequently be reduced to provide a snug fit or adhesion of the device to the fixed tissue. The space could be reduced, for example, by drawing, pulling, or otherwise gathering a portion of the suture 12 to reduce the total length of the suture. For example, the ends of the suture could both be pulled in a direction tending away from the securing elements 14, 16. This would tend to reduce the space between the securing elements 14, 16 and the third portion 30 of the suture 12.

FIG. 1 shows the first securing element 14 and the second securing element 16 in a first position that is oriented and positioned to facilitate deployment of the tissue fixation device 10 into, e.g., a subject. The elements 14, 16 can be oriented substantially perpendicular to the plane of tissue into which the device 10 is to be deployed and substantially parallel to the holes that are created in the tissue and through which the securing elements 14, 16 may pass. This first position facilitates deployment because it presents the smallest surface area of securing elements 14, 16. An orientation in the first position can, among other things, minimize trauma to the tissue, minimize the amount of force required to penetrate the tissue, and create the smallest defect in the tissue possible.

FIG. 2 shows the first securing element 14 and the second securing element 16 in a second position that is oriented and positioned to fix the device 10 securely with respect to the tissue. The securing elements 14, 16 can be oriented substantially perpendicular to the first position and to the holes through which the securing elements 14, 16 pass. For example, if the securing elements 14, 16 have an elongated shape such that the long axis of the securing element is larger than the diameter of the hole, then the long axis of the securing element can be oriented perpendicular to the hole, thereby hindering return of the securing element through the hole. Exemplary dimensions of a securing element include from about 2 to about 20 mm long, preferably about 4-6 mm long, more preferably about 4.2 mm long; and about 1 mm to about 5 mm in diameter, preferably about 1 mm to about 2 mm in diameter; more preferably about 1.2 mm in diameter. The second position facilitates fixation of the device, by it inhibiting the securing elements 14, 16, from passing back through the holes created in the tissue. If tension develops in the suture 12, tending to draw the securing elements 14, 16 through the holes, then the perpendicular orientation of securing elements 14, 16 relative to the holes can tend to prevent such passage. The second position also can maximize the surface area of the securing elements 14, 16 in contact with the tissue, thereby distributing forces exerted on or by the securing elements 14, 16 over the largest area of the tissue. Orientation in the second position can limit trauma to the tissue by minimizing pressure delivered to a particular point on the tissue surface or interior. The second position can also decrease the amount of shear stress of the suture and chafing of the suture by the securing elements 14, 16, because the portions 18, 20, and the loops 26, 28 will be oriented substantially orthogonal with respect to the securing elements 14, 16.

In the exemplary embodiment illustrated in FIGS. 1 and 2, the tissue fixation device 10 includes a first pledget 24. Portions of suture 12 may pass through holes 32 of the first pledget 24. When the device 10 is deployed, the tissue to be fixed can be positioned between the first pledget 24 and the securing elements 14, 16 with strands of the suture 12 passing through holes in the tissue. For embodiments in which the suture 12 has two ends (such as described above for third portion 30), the ends may be disposed on the same side of the first pledget 24.

The first pledget 24 may further facilitate tissue fixation by providing a larger surface of contact between the device 10 and the tissue. This increased surface area may also help to minimize tissue trauma by further distributing forces and pressures impinging on the device 10, one or more of its components, or the tissue. In an embodiment, the first pledget 24 may include a soft material, a malleable material, a pliable material, a resorbable material, a bioabsorbable material, a nonresorbable material, a radio-opaque material, or an adhesive material, or various combinations thereof. Exemplary material that may form the pledget at least in part include polytetrafluoroethylene (PTFE), PTFE felt, polyglycolic acid (PGA) felt, and polylactic acid (PLA) felt. The first pledget 24 may be manufactured by, for example, injection molding, by die-cutting, and/or by laser cutting, or by a variety of other cutting and molding techniques. The first pledget 24 may have a variety of shapes. For example, the pledget may be generally parallelepiped in shape; may have rounded corners; may have sharp corners; and/or may be generally disc shaped. In an embodiment, the pledget may have dimensions of about 1 mm to about 10 mm long, preferably about 6 mm; about 1 mm to about 10 mm wide, preferably about 4 mm; and about 0.5 to about 5 mm thick, preferably about 1 mm. The location of the first pledget 24 is not limited to the position illustrated. For example, the first pledget 24 may be located further distally along the strands of suture 12. The first pledget 24 may be located adjacent to the securing elements 14, 16 such that it is located on the distal side of tissue to be fixated.

Figure 3:
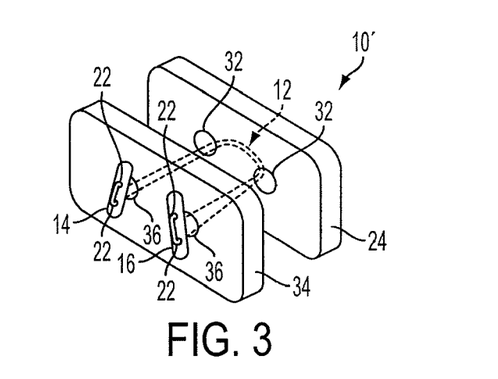
FIG. 3 is perspective view of another exemplary embodiment of a tissue fixation device including a first and a second pledget.

FIG. 3 depicts another exemplary embodiment of a tissue fixation device 10' further including a second pledget 34. A portion of suture 12 can loop through holes 32 of the first pledget 24, through holes 36 of the second pledget 34, and/or through holes 22 in the first and second securing elements 14, 16, thereby connecting the first and second securing elements 14, 16 to the first pledget 24 and to the second pledget 34. First and second pledgets 24, 34, may be spaced apart to facilitate tissue therebetween, as described for other embodiments.

The second pledget 34 may improve tissue fixation and minimize tissue trauma in ways similar to those for the first pledget 24. It may also include similar materials to those of the first pledget 24. It may have the same dimensions as the first pledget 24 or have dimensions different from the first pledget 24. For example, if two surfaces of a tissue to be fixated have different dimensions, then first and second pledgets 24, 34 may be dimensionally adapted to correspond to those dimensions. Such adaptation would tend to maximize surface contact between each pledget and its respective tissue surface without introducing waste or overhang of pledget material.

The second pledget 34 may be positioned in physical contact with securing elements 14, 16, as illustrated in FIG. 3. The securing elements 14, 16, may be oriented in the first position, e.g., during deployment, such that they can be readily passed through the holes 32, 36 of the first and second pledgets 24, 34, and also through holes in the tissue being affixed. The securing elements 14, 16, may be oriented in the second position such that they are perpendicular to the holes 36 and thereby inhibited from passing therethrough.

Figure 4:
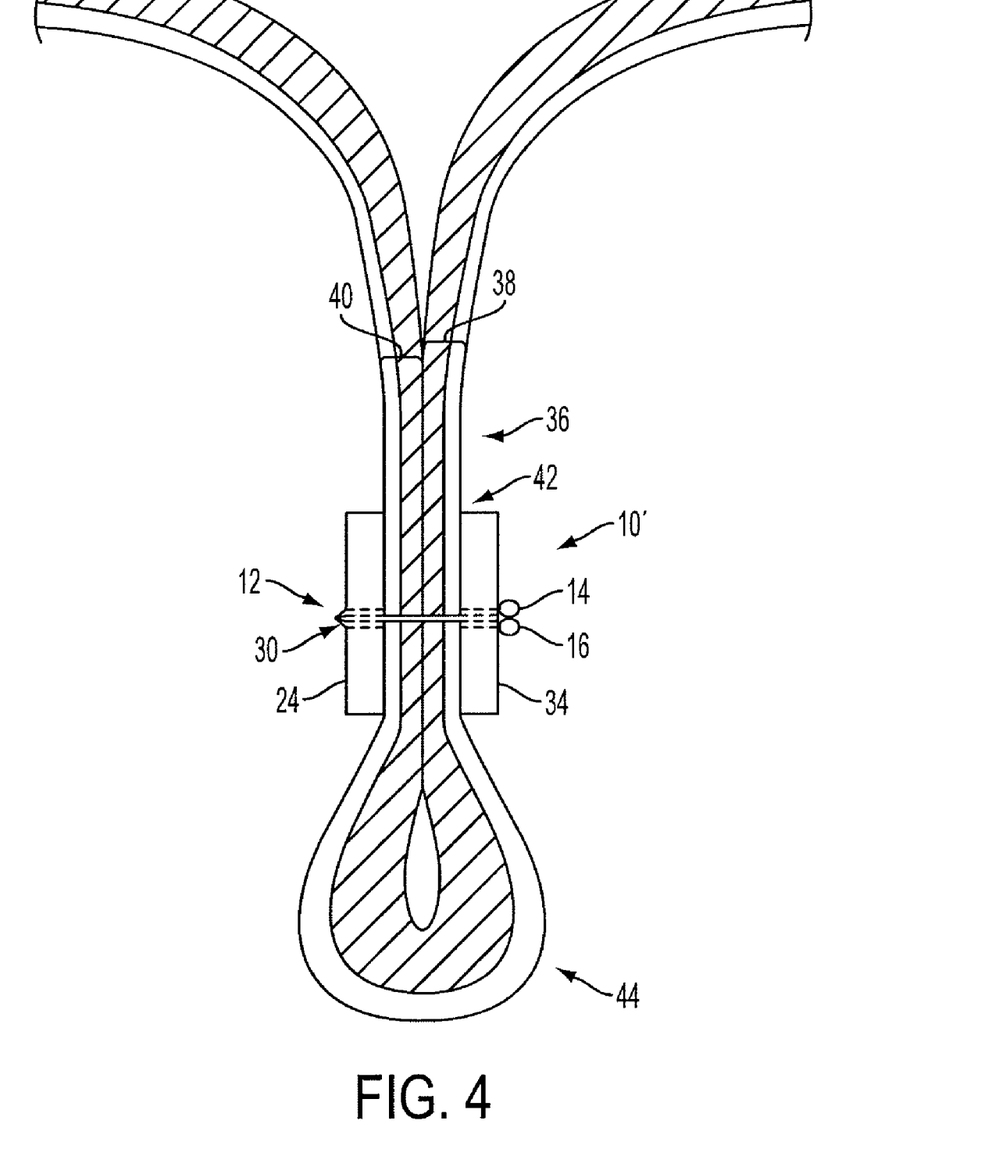
FIG. 4 is a side elevational view in cross-section of the tissue fixation device of FIG. 3, illustrating the device deployed to anchor a portion of the tissue.

FIG. 4 illustrates an embodiment of the device 10' having first and second pledgets 24, 34, that has been deployed to fixate tissue 36. The first pledget 24 and third portion 30 of the suture 12 are positioned to one side of the tissue 36. The second pledget 34 and the securing elements 14, 16, are positioned on the other side of tissue 36. The securing elements 14, 16 are shown end-on in FIG. 4. The tissue 36 may include one or more layers. For example, as depicted in FIG. 4, the tissue 36 can be folded back upon itself, forming two layers 38, 40, and thereby creating a plication 42, and, optionally, a bulge 44. While a tool is employed to hold the tissue 36 in this plicated state, holes are created in the layers 38, 40, and the device 10 is deployed on the tissue 36, such that the securing elements 14, 16 are oriented in the first position and advanced from one side of the plication 42, through the holes, and to the other side of the plication 42. The securing elements 14, 16 are then oriented in the second position to prevent them from slipping back through the holes in the tissue 36. In alternative embodiments, the device further includes one or both of the first pledget 24 and the second pledget 34, deployed, respectively, on either side of the plication 42.

Figure 5:
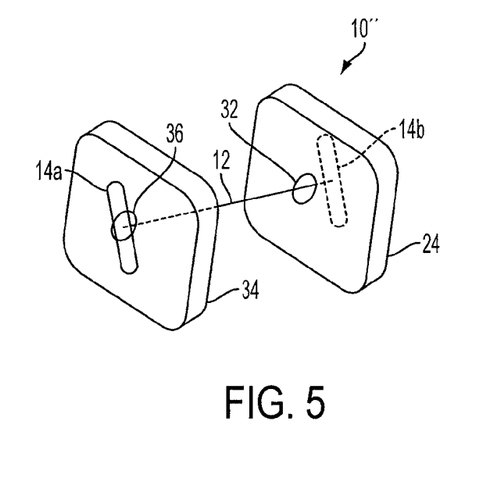
FIG. 5 is a perspective view of another exemplary embodiment of a tissue fixation device.
Figure 6:
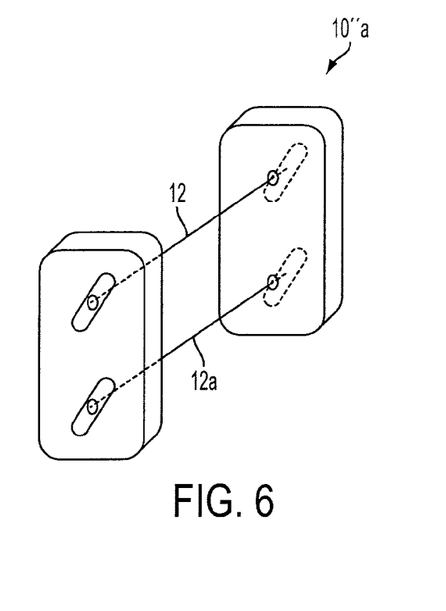
FIG. 6 is a perspective view of another exemplary embodiment of a tissue fixation device.

FIG. 5 depicts another exemplary embodiment of a tissue fixation device 10" having a suture 12, a first pledget 24 with at least one hole 32 formed therein, a second pledget 34 with at least one hole 36 formed therein, and first and second securing elements 14a, 14b. The securing elements 14a, 14b may be connected to portions of the suture 12, such as end portions. The suture 12 may be connected to securing elements 14a, 14b as described above, such as by looping through holes (not shown) in securing elements 14a, 14b. At least one securing element 14a may be rotatable from a first position in which the securing element is oriented to pass through the respective pledget hole (i.e., parallel or substantially parallel) to a second position in which the securing element is oriented not to pass through the pledget hold (i.e., nonparallel, preferably perpendicular or substantially perpendicular). FIG. 6 depicts a related exemplary embodiment of a tissue fixation device 10"a having a second suture 12a.

Figure 7:
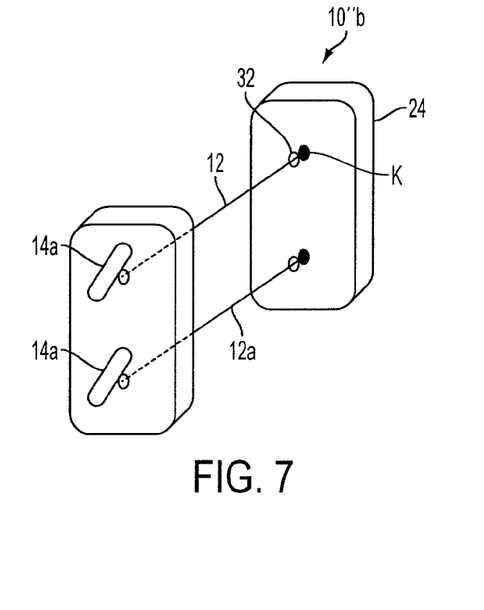
FIG. 7 is a perspective view of another exemplary embodiment of a tissue fixation device.

FIG. 7 depicts yet another exemplary embodiment of a tissue fixation device 10"b having a securing element 14a connected to a portion of suture 12. Another portion of suture 12 may pass through the at least one hole 32 in the first pledget 24, while a further portion K of the suture may be configured to inhibit portion K of the suture 12 from passing through the at least one hole 32. Portion K may be, for example, a knot. The knot may be sized and/or shaped to prevent it from passing through hole 32. The embodiment depicted in FIG. 7 includes two sutures. However, an alternative embodiment have only one suture.

Figure 8:
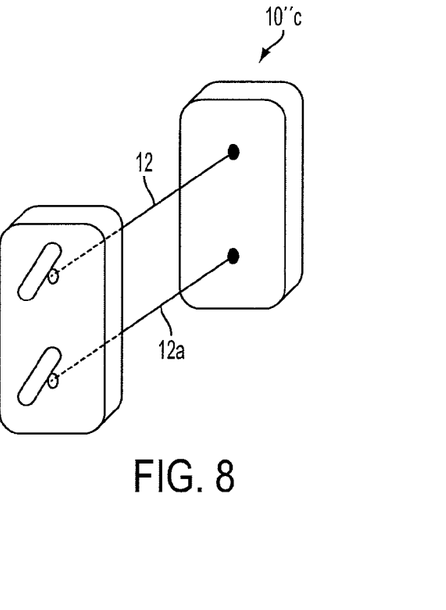
FIG. 8 is a perspective view of another exemplary embodiment of a tissue fixation device.

FIG. 8 depicts still another exemplary embodiment of a tissue fixation device 10"c in which sutures 12, 12a are connected to first pledget 24. A suture may be connected to the pledget by, for example, welding, gluing, melting, and/or embedding. The embodiment depicted in FIG. 8 includes two sutures. However, an alternative embodiment have only one suture.

The amount of tissue 36 to include in the plication 42 may be chosen so as to control the distance that the plication 42 extends from the customary surface of the tissue 36. The amount of tissue and also the positioning of the device 10 along the plication 42 may also be chosen so as to control the size of the bulge 44 created thereby.

Figure 9:
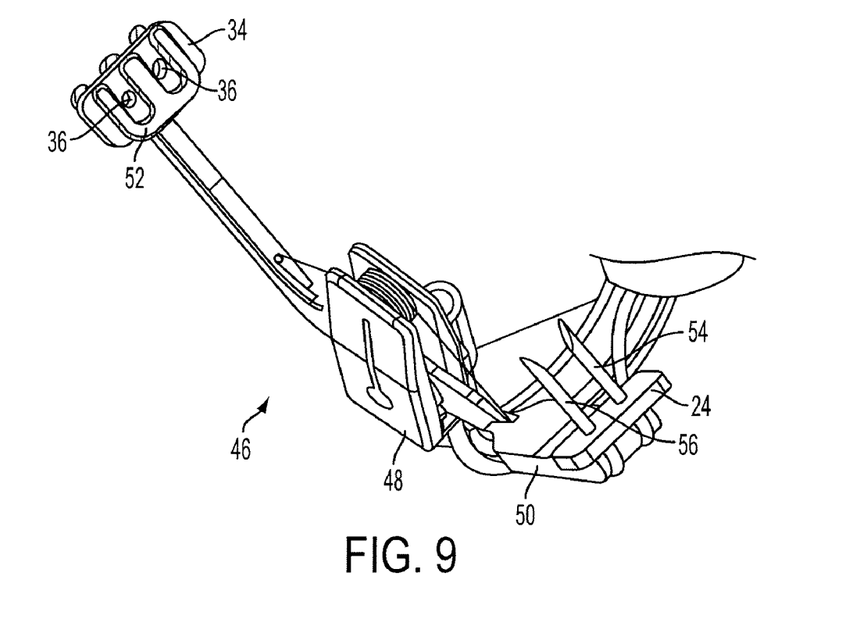
FIG. 9 is a perspective view of an exemplary instrument for deploying a tissue fixation device.

FIG. 9 depicts, among other things, a portion of an exemplary apparatus 46 for deploying the tissue fixation device 10. The apparatus 46 is described in detail in copending U.S. patent application Ser. No. 09/859,579, filed May 18, 2001, incorporated herein by reference. The apparatus 46 has a mount 48 from which emerges a first jaw 50 and a second jaw 52. The jaws 50, 52 may swing radially from pivots in the mount 48. Upon the first jaw 50 may be mounted the first pledget 24. Upon the second jaw may be mounted the second pledget 34. During deployment, the jaws 50, 52 may be swung together so that they are brought into axial alignment on opposite sides of a tissue to fix.

Figure 10:
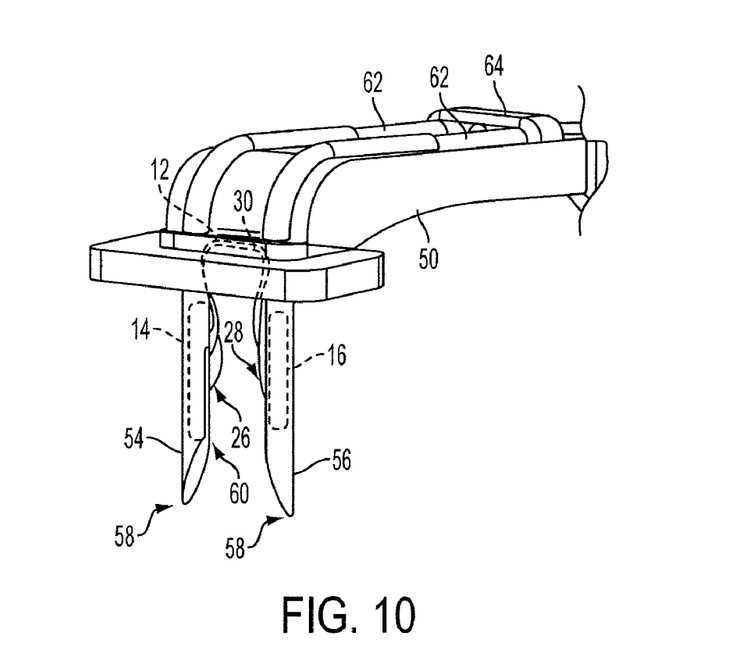
FIG. 10 is a perspective view of a jaw member of the instrument of FIG. 9.

FIG. 10 shows the first jaw 50 of the apparatus 46 in greater detail. The first jaw 50 can include two tubes 54, 56. The tubes 54, 56 may be provided with sharp ends 58 suitable for piercing tissue. The ends 58 may include a variety of materials suitable for piercing tissue, such as surgical carbon steel or plastic. The ends 58 may be beveled or angled to facilitate piercing of particular types of tissue. The first pledget 24 can be mounted on the first jaw 50 by threading the tubes 54, 56 through the holes 32 of the first pledget 24.

The securing elements 14, 16 can be positioned inside the tubes 54, 56. The loops 26, 28 of suture 12 can emerge from the tubes 54, 56 through ends 58 in the tubes 54, 56 The strands of the suture 12 may then pass through the holes 32 of the first pledget 24 and terminate in the third portion 30 of the suture 12.

In an exemplary embodiment, the tissue fixation device may be deployed by positioning the apparatus 46 around a fold of tissue, swinging the jaws 50, 52 to bring them into axial apposition on opposing sides of the tissue fold. As this occurs, ends 58 of the tubes 54, 56 pierce the tissue, penetrating it and creating holes in the tissue. As the tubes 54, 56 emerge through the other side of the tissue, they engage the second jaw 52. In an embodiment, they pass through holes 36 of the second pledget 34. The securing elements 14, 16, in the first position, are then advanced through the tubes 54, 56 and the holes in the tissue, ultimately emerging on the opposite side of the tissue. The securing elements 14, 16 may then be reoriented into the second position. In an embodiment, the securing elements 14, 16 are advanced by push rods 62 that are pushed through the tubes 54, 56 by a push bar 64.

Figure 11:
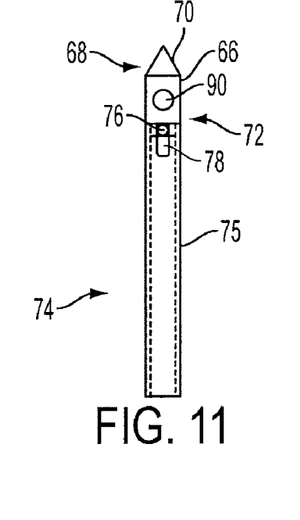
FIG. 11 is a side elevational view of an alternate embodiment of the securing element of an exemplary tissue fixation device.

FIG. 11 depicts an alternate embodiment of a securing element that can be removably coupled to the tubes or to some other component of a tissue fixation device or system. As shown in FIG. 11, a first securing element 66 having a distal end 68 which includes a sharp tip 70. The first securing element 66 also has a proximal end 72 which can be removably attached to a deployment instrument 74. Deployment instrument 74 may include a tube 75. The proximal end 72 can have a nub 76 that is slidably received in a slot 78 of deploying instrument 74. The first securing element 66 can be integrally coupled to the deployment instrument 74. The first securing element 66 can have a hole or opening 90 through which a second portion (not shown) of a suture (not shown) is coupled to the first securing element 66. The suture can have a proximal portion that affixes a proximal side of a tissue to be fixated during deployment. The suture can, alternatively, be glued to, welded to, embedded in, melted onto, stapled to, or otherwise attached, connected, or coupled to the first securing element 66.

FIG. 11 depicts an exemplary embodiment of a tissue fixation device including a first securing element 66 that is configured to separate from the deployment instrument 74 during deployment. The first securing element 66 can be integrally molded. The first securing element 66 can include metal. The deployment instrument 74 can include plastic. The deployment instrument 74 can be integrally molded. The first securing element 66 can be insert molded into the tube 75. The tissue fixation device may include a second securing element (not shown). The second securing element can be integrally molded. The second securing element can include metal. The suture may be coupled to the second securing element, as described above.

Figure 12:
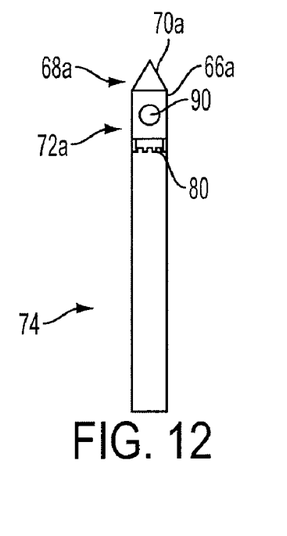
FIG. 12 is a side elevational view of another alternate embodiment of the securing element of an exemplary tissue fixation device.

FIG. 12 depicts another exemplary embodiment in which the first securing element 66a is configured to be integrally coupled to the deploying instrument 74 and to separate from the deployment instrument 74 during deployment. In FIG. 12, the first securing element 66a has a distal end 68a which includes a sharp tip 70a, and a proximal end 72a which has an undercut 80 that releasably attaches the first securing element 66a to the deployment instrument 74 and also determines the force necessary to separate the first securing element 66a from the deployment instrument 74. A second securing element (not shown) can be provided having a distal end with a sharp tip, and a proximal end with an undercut that releasably attaches the second securing element to the deployment instrument 74 and also determines the force necessary to separate the second securing element from the deployment instrument 74. A suture as described above may be coupled to the first securing element 66a and/or second securing element through hole 90. The suture may be similarly coupled to the second securing element.

Figure 13:
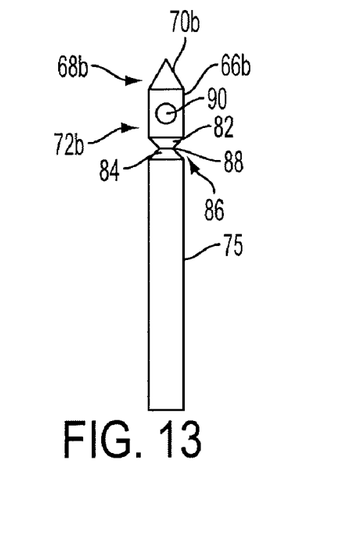
FIG. 13 is a side elevational view of a further alternate embodiment of the securing element of an exemplary tissue fixation device.

FIG. 13 depicts another exemplary embodiment of a tissue fixation device in which the proximal end 72b of the first securing element 66b includes a reduced diameter portion 82 that releasably couples the first securing element 66b to the deployment instrument 74. The first securing element 66b has a distal end 68b which includes a sharp tip 70b. The deployment instrument 74 can include a tube or shaft 75 having a reduced diameter portion 84 at its distal end 86. The first securing element 66b and the tube 75 can be formed of a metal or of a uniform material. The first securing element 66b and the tube 75 may be integrally molded. The junction 88 of reduced diameter portions 82, 84 can be designed to break upon application of a predetermined force. The junction 88 can be designed to break upon application of a force that is more than the force needed to push the first securing element 66b through tissue to be fixated, thereby ensuring that the securing element 66b does not break off of the tube 75 before the securing element 66b is pushed completely through the tissue. The tissue fixation device may further include a second securing element, having a distal end with a sharp tip. The deployment instrument 74 may include a second tube or shaft (not shown) having a reduced diameter portion at its distal end. The second securing element and the second tube can be formed of a metal or of a uniform material. The second securing element and the second tube may be integrally molded. The first securing element 66b, the tube 75, the second securing element, and the second tube may be integrally molded. A suture as described above may be coupled to the first securing element 66a and/or second securing element through hole 90. The suture may be similarly coupled to the second securing element.

The first securing elements 66, 66a, 66b, and the second securing elements can each be configured to secure a tissue fixation device to a distal side of a tissue to be fixated. The first and second securing elements can be secured to a suture that is coupled to one or more of the securing elements through the hole 90. The first securing elements and/or second securing elements can be rotatable from a first position that is suitable for each securing element to pass through a respective hole formed in the tissue to a second position that inhibits each securing element from passing through the respective hole formed in the tissue.

Figure 14:
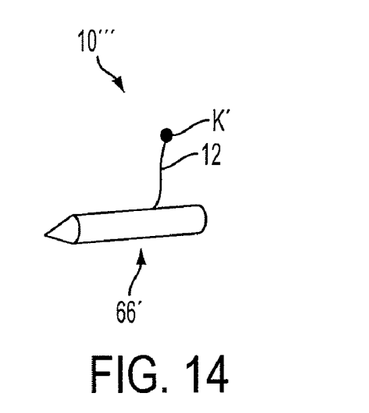
FIG. 14 is a perspective view of another exemplary embodiment of a tissue fixation device.

FIG. 14 depicts an embodiment of a tissue fixation device 10''' having a suture 12 and a securing element 66' such as those depicted in FIGS. 11, 12, and/or 13. The securing element 66'' may be coupled to the suture as described above. The suture may have a proximal portion K' that may be configured, such as sized and/or shaped, to secure the tissue fixation device at a proximal side of a portion of tissue so that the tissue is fixed between the securing element 66' and the proximal portion K' of the suture 12 during deployment of the device. For example, portion K may be a knot as described previously.

A tissue fixation device having securing elements such as those depicted in FIG. 11, 12, or 13 can also have a first pledget (not shown). The pledget can have at least one hole through which a suture passes. The tissue fixation device can also have a second pledget. The second pledget can have at least one hole through which the suture can pass. In an embodiment, the first and second pledgets are spaced apart from one another with the tissue to be fixated positioned therebetween when the device is deployed.

Securing elements such as those depicted in FIG. 11, 12, or 13, can be integrally coupled to the deployment instrument 74 and configured to separate from the instrument 74 during deployment.

Figure 15:
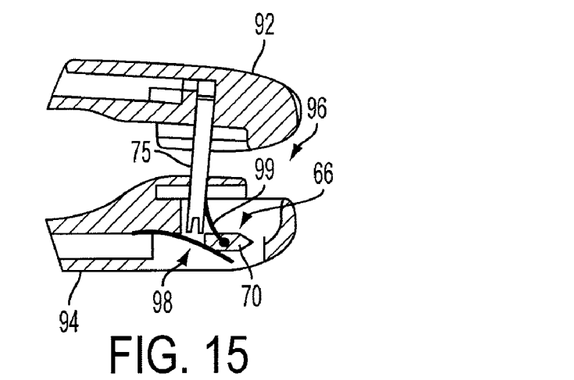
FIG. 15 is a side elevational view in cross section of an exemplary instrument for deploying a tissue fixation device.

FIG. 15 depicts in cross section a portion of an instrument for deploying a tissue fixation device. The instrument is described in detail in copending U.S. patent application Ser. No. 09/859,579, filed May 18, 2001, incorporated herein by reference. During deployment, arms 92, 94 are brought into apposition. Tube 75 is coupled to first arm 92. A first securing element (in this exemplary embodiment, 66) is releasably coupled to tube 75. Tissue to be fixated is positioned in space 96 between arms 92, 94. As the arms are drawn together, the sharp tip 70 pierces the proximal side of the tissue and forms a hole therethrough. The securing element 66 emerges on the distal side of the tissue and contacts the second arm 94. The second arm 94 can include a separation device 98 that causes the securing element 66 to separate from tube 75. When the securing element contacts the separation device 98, the separation device 98 imparts, e.g., a lateral force to the securing element and causes it to separate from the tube 75. A suture 99 may be coupled to the securing element 66. In the exemplary embodiment depicted in FIG. 15, the separation device 98 includes a spring member. When the securing element 66 contacts the flexible member, the spring member bends, thereby applying a lateral force to the securing element 66. The lateral force may also facilitate the orienting of the securing elements from the first position to the second position.

In an embodiment, after the securing elements have been separated from the tubes, the arms 92, 94 can be separated or drawn apart from one another, withdrawing the tube 75 from the tissue and allowing the instrument to be removed from the tissue.

Figure 16:
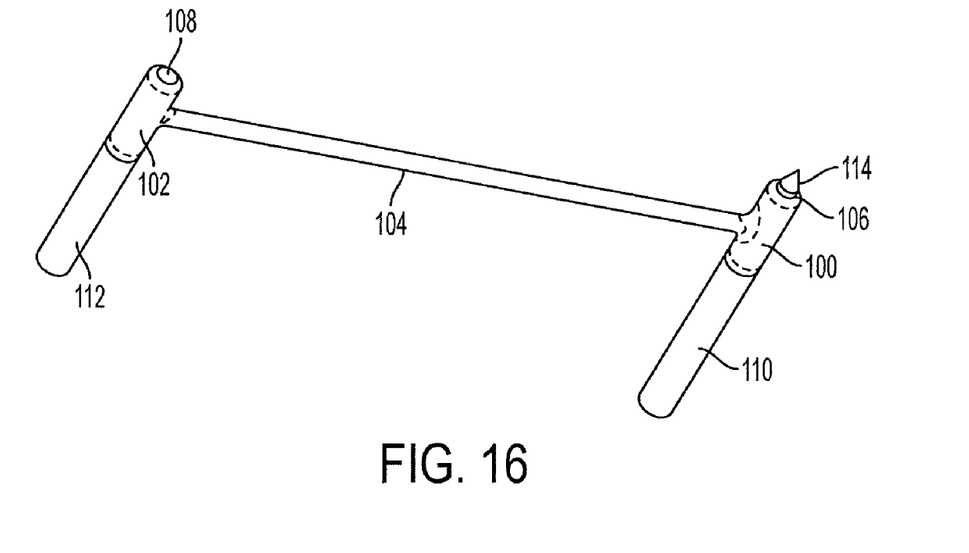
FIG. 16 is a perspective view of a further exemplary embodiment of a tissue fixation device, illustrating one securing element of the tissue fixation device mounted to an exemplary deployment instrument.

FIG. 16 depicts an exemplary embodiment in which securing elements 100, 102 are connected by a flexible spanning member 104 instead of by a suture. The securing elements 100, 102, define bores 106, 108 and are received on members 110, 112 having tissue penetrating tips 114. The members 110, 112 may be advanced through tubes 54, 56, as described above. In an embodiment, the securing elements 100, 102 are advanced, in the first position described previously, through respective holes in tissue that are created as tissue penetrating tips 114 pass through the tissue. Securing elements 100, 102 can emerge on a distal side of the tissue to be fixated and rotated to the second position. The members 110, 112 may then be withdrawn through the bores 106, 108, leaving the securing elements 100, 102 attached to the distal side of the tissue. The flexible spanning member 104 may be attached to a proximal side of the tissue to be fixated.

Figure 17:
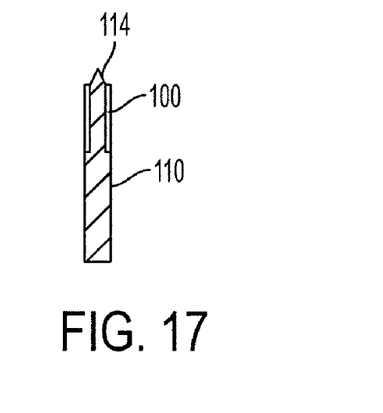
FIG. 17 is a side elevational view in cross-section of a securing element of the tissue fixation device of FIG. 16, illustrating the securing element mounted to the exemplary deployment instrument.

FIG. 17 depicts in cross section a securing element 100 received on member 110 having tissue penetrating tip 114. As shown in this figure, the member 110 (also member 112) can have a region of decreased diameter configured to be received within the bore 106 of the securing element 100. The tightness of the fit between the bore 106 and the member 110 can be determined to control the amount of force necessary to remove the member 110 from within the securing element 100. In another embodiment, the member 110 can be coupled to the securing element by a perforated connection. The shear caused by withdrawal of the member 110 can tear apart the perforation and thereby release the member 110 from the securing element 100. In yet another embodiment, the member 110 can be releasably glued, spot-welded, melted, or otherwise attached to securing element 100 so as to necessitate the application of a preselected amount of force in order to remove the member 110 from the securing element 100.

Figure 18:
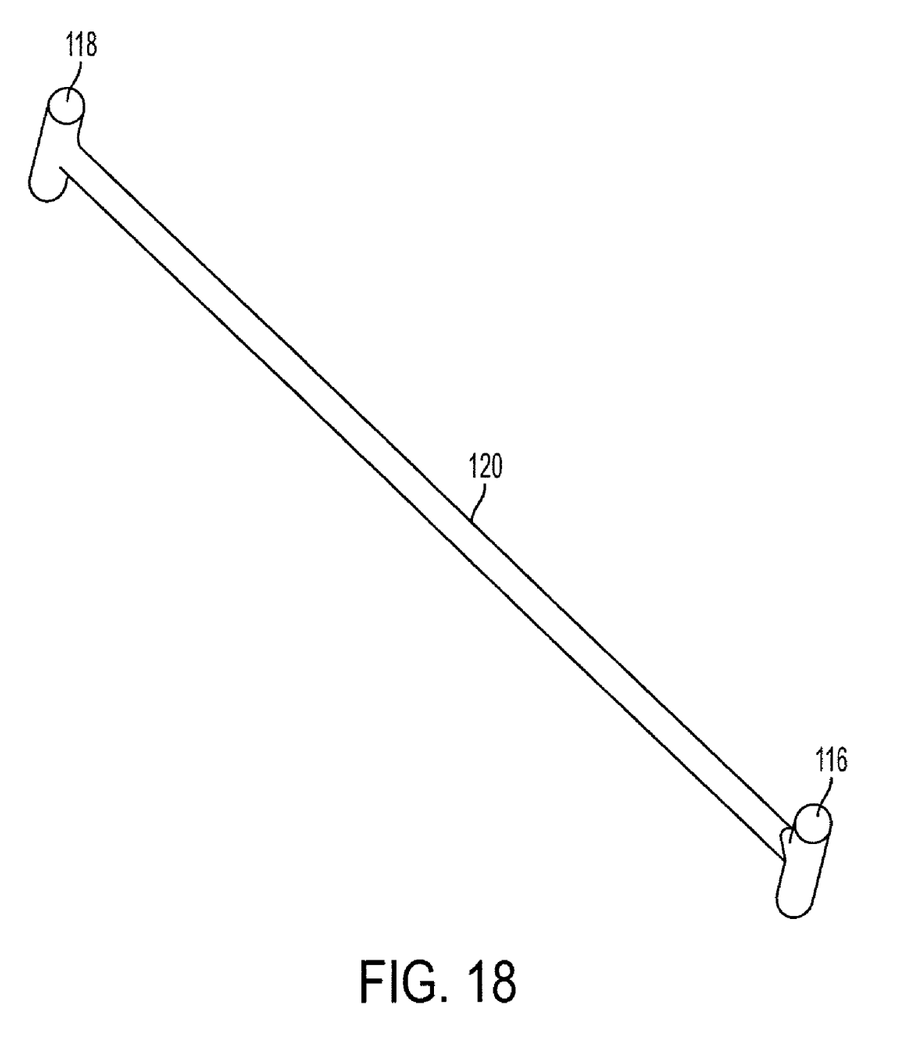
FIG. 18 is a perspective view of another exemplary embodiment of a tissue fixation device.

FIG. 18 depicts another embodiment of a tissue fixation device, in which securing elements 116, 118 are connected by a flexible spanning member 120. During deployment, the securing elements may be deployed inside, e.g., the tubes 54, 56 of FIG. 10. The sharp ends 58 of the tubes 54, 56 create respective holes in the tissue to be fixated. The securing elements 116, 118 pass through the tubes and are deposited on the distal surface of the tissue to be fixated, as described above.

Because certain changes may be made in the above constructions without departing from the scope of the present disclosure, it is intended that all matter contained in the above description or shown in the accompanying drawings be interpreted as illustrative and not in a limiting sense.

It is also to be understood that the following claims are to cover all generic and specific features of the devices and methods described herein.

What is claimed is:

1. A tissue fixation device comprising:
   a suture;
   a first bioimplantable pledget having at least one through hole formed therein having a minimum diameter greater than a maximum diameter of the suture, a first portion of the suture passing through the at least one through hole in the first pledget and a second portion of the suture configured to inhibit the second portion from passing through the at least one through hole in the first pledget;

a second bioimplantable pledget having at least one through hole formed therein, the first pledget being spaced apart from the second pledget to receive tissue therebetween when the tissue fixation device is deployed;

a first bioimplantable securing element connected to a portion of the suture, the first securing element being rotatable from a first orientation in which the securing element is oriented at least substantially parallel to the at least one through hole formed in the first pledget and the second pledget, to a second orientation in which the securing element is oriented at least substantially perpendicular to the at least one through hole in the second pledget, wherein the suture, the first and second pledgets, and the first securing element are effective to fix adjacent layers of living tissue.

2. The tissue fixation device of claim 1, further comprising a second suture and a second bioimplantable securing element connected to a portion of the second suture.

3. The tissue fixation device of claim 2, wherein a first portion of the second suture passes through a second through hole in the first pledget and a second portion of the suture is configured to inhibit the second portion of the suture from passing through the second through hole in the first pledget.

4. The tissue fixation device of claim 3, wherein the second securing element is rotatable from a first position in which the second securing element is oriented at least substantially parallel to the second through hole in the first pledget and a second through hole in the second pledget to a second position in which the securing element is oriented at least substantially perpendicular to the second through hole in the second pledget.

5. The tissue fixation device of claim 2, wherein said second suture comprises a material suitable for suturing human or animal tissue in vivo, and said second securing element comprises biocompatible material.

6. The tissue fixation device of claim 1, wherein said suture comprises a material suitable for suturing human or animal tissue in vivo, and said securing element comprises biocompatible material.

7. A tissue fixation device comprising:

a suture suitable for in vivo placement in a human body;

a first biocompatible securing element connected to a first portion of the suture;

a second biocompatible securing element connected to a second portion of the suture, each said first and second securing elements being rotatable from a first position during deployment of the tissue fixation device that is suitable for each securing element to pass through a respective hole formed in human or animal tissue to a second position substantially perpendicular to the first position when the tissue fixation device is deployed that inhibits each securing element from passing through the respective hole formed in said tissue;

a deployment instrument having first and second tubes configured to deliver the first and second securing elements in the first position through the tubes and through the respective hole formed in said tissue;

a first pledget having a plurality of through holes formed therein, the suture passing through the through holes in the first pledget; and a second pledget having a plurality of through holes formed therein, the suture passing through the through holes in the second pledget, the second pledget being spaced apart from the first pledget when the tissue fixation device is deployed.

8. The tissue fixation device of claim 7, wherein the first and second securing elements are spaced apart from a third portion of the suture when the tissue fixation device is deployed, the human or animal tissue being fixed between the securing elements and the third portion during deployment.

9. The tissue fixation device of claim 8, wherein a portion of the suture is coupled to another portion of the suture.

10. The tissue fixation device of claim 9, wherein the portions are coupled by knotting.

11. The tissue fixation device of claim 9, wherein the portions are coupled by welding.

12. The tissue fixation device of claim 9, wherein the first portion of the suture passes through openings in the first securing element.

13. The tissue fixation device of claim 12, wherein the second portion of the suture passes through openings in the second securing element.

14. The tissue fixation device of claim 7, wherein the suture passes through the through holes as to enable the first pledget to be positioned between the first and second securing elements and the tissue when the tissue fixation device is deployed.

15. The tissue fixation device of claim 7, wherein the suture has two ends, and both ends are disposed on the same side of the first pledget.

16. The tissue fixation device of claim 7, wherein the first securing element and the second securing element are oriented at least substantially parallel to the holes in the tissue in the first position.

17. The tissue fixation device of claim 7, wherein the first securing element and the second securing element are oriented at least substantially perpendicular to the holes in the tissue in the second position.

18. The tissue fixation device of claim 7, wherein the first securing element and the second securing element are each generally cylindrical in shape.

19. The tissue fixation device of claim 7, wherein each said first securing element and second securing element includes a sharp tip.

20. The tissue fixation device of claim 7, wherein each said first securing element and second securing element have an elongated shape such that the long axis of the securing element is larger than the diameter of the respective hole.

21. The tissue fixation device of claim 7, wherein the suture is endless.

22. The tissue fixation device of claim 7, wherein the suture forms a closed loop.

23. A tissue fixation device comprising:

a suture;

a first bioimplantable pledget having a plurality of through holes formed therein, the suture passing through the through holes in the first pledget;

a second bioimplantable pledget having a plurality of through holes formed therein, the first pledget being spaced apart from the second pledget to receive tissue therebetween when the tissue fixation device is deployed;

a first bioimplantable securing element having a sharp tip and a proximal end configured for removable attachment to an instrument, the first securing element being coupled to the suture; and a second bioimplantable securing element having a sharp tip and a proximal end configured for removable attachment to an instrument, the second securing element being coupled to the suture, wherein the suture, the first and second pledgets, and the first and second securing elements are effective to fix adjacent layers of living tissue.

24. The tissue fixation device of claim 23, wherein said suture comprises a material suitable for suturing human or animal tissue in vivo, and said first and second securing elements comprise biocompatible material.

* * * * *